United States Patent
Furfine et al.

(10) Patent No.: US 6,811,780 B2
(45) Date of Patent: Nov. 2, 2004

(54) METHODS OF USING CYTOKINE ANTAGONISTS TO TREAT HIV INFECTION AND AIDS

(75) Inventors: Eric S. Furfine, Croton-on-Hudson, NY (US); Neil Stahl, Carmel, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 0 days.

(21) Appl. No.: 10/427,863

(22) Filed: May 1, 2003

(65) Prior Publication Data

US 2003/0211104 A1 Nov. 13, 2003

Related U.S. Application Data

(60) Provisional application No. 60/377,260, filed on May 1, 2002, and provisional application No. 60/426,270, filed on Nov. 14, 2002.

(51) Int. Cl.$^7$ ............................................. A61K 39/395
(52) U.S. Cl. ............................... 424/145.1; 424/158.1; 424/178.1; 424/278.1; 530/388.23; 530/389.2
(58) Field of Search .................. 530/388.23, 389.2; 424/145.1, 158.1, 178.1, 278.1

(56) References Cited

U.S. PATENT DOCUMENTS 6,328,954 B1   12/2001   Enssle et al.

FOREIGN PATENT DOCUMENTS

| WO | WO 00/18932 | 4/2000 |
| WO | WO 01/92340 | 12/2001 |
| WO | WO 02/04009 | 1/2002 |

OTHER PUBLICATIONS

Denis, et al., Aids Research and Human Retroviruses, vol. 10, No. 7 (1994) pp. 795–802.
Mikovits, et al., Journal of Leukocyte Biology, vol. 56, pp. 340–346 (1994).
Naif, et al., The Journal of Immunology, vol. 158, No. 1, pp. 501–511, (1977).
Zou et al, AIDS, vol. 11, No. 4, pp. 533–534 (1997).
Montaner et al., Journal of Leukocyte Biology, vol. 62, No. 1, pp. 126–132 (1997).
Marshall et al., Journal of Immunology, vol. 159, No. 11, pp. 5705–5714 (1997).
Kim et al., Journal of Interferon and Cytokine Research, vol. 20, No. 3, pp. 311–319, (2000).

*Primary Examiner*—Jeffrey Stucker
(74) *Attorney, Agent, or Firm*—Valeta Gregg, Esq.

(57) ABSTRACT

The invention is methods of using cytokine antagonists to treat HIV. In particular, the invention is methods of treating HIV using L-4 and IL-13 cytokine antagonists, including cytokine traps and anti-IL-4 or anti-IL-13 antibodies. The invention also includes augmenting the efficacy of HIV vaccination by co-administration of the vaccine with IL-4 and IL-13 cytokine antagonists.

13 Claims, 2 Drawing Sheets

METHODS OF USING CYTOKINE ANTAGONISTS TO TREAT HIV INFECTION AND AIDS

This application claims the benefit of U.S. Provisional Application No. 60/377,260, filed May 1, 2002, and U.S. Provisional Application No. 60/426,270, filed Nov. 14, 2002, the contents of which are incorporated herein by reference.

FIELD OF THE INVENTION

The field of the invention is methods of using cytokine antagonists to treat HIV infection and AIDS. In particular, the field of the invention is methods of treating HIV infection and AIDS using IL-4/IL-13 cytokine antagonists. The field of the invention also includes augmenting the efficacy of HIV vaccines by co-administration with IL-4/IL-13 cytokine antagonists.

BACKGROUND

AIDS (acquired immune deficiency syndrome) is caused by the human immunodeficiency virus (HIV). Most scientists think that HIV causes AIDS by directly killing CD4$^+$T cells or interfering with their normal function, and by triggering other events that weaken a person's immune function. It is widely thought that the HIV-specific cytotoxic T-lymphocytes (CTL) and T-helper cells play a central role in the control of viral replication (Reviewed by Ghandi and Walker 2002 Annu Rev Med 2002;53:149–72; Altfeld and Walker 2001 nature Medicine 8(7) 881–884). In addition, neutralizing antibodies play an apparently subordinate role in viral control (Poignard P et al. 1999 Immunity 10, 431–438). In fact, HIV elicits primarily a non-neutralizing antibody response in vivo that may provide a mechanism of immune escape (C. Grundner et al. 2002 9$^{th}$ Conference on Retroviruses and Opportunistic Infections, February 24–28, Abstract 105).

A number of drugs for the treatment of HIV infection have been approved over the past ten years. These drugs include nucleoside analog reverse transcriptase inhibitors (NRTIs), which interrupt an early stage of viral replication. Included in this class of drugs are zidovudine (AZT), didanosine (ddI), stavudine (D4T), lamivudine (3TC) and abacavir succinate. These drugs reduce the systemic viral load resulting from HIV infection and proliferation and thus reduce the frequency of opportunistic infections. Importantly, they do not prevent transmission of HIV to other individuals, though they do likely reduce the rate of transmission. Non-nucleoside reverse transcriptase inhibitors (NNRTIs) such as nevirapine and efavirenz are also available for use in combination with other antiretroviral drugs. Another class of drugs is called protease inhibitors, which interrupt viral replication at a later step in its life cycle. They include ritonavir, saquinivir, indinavir, amprenavir, lopinavir, and nelfinavir. Finally, a brand new class of drug called a fusion inhibitor has just been approved for use (T-20 or fuzeon). Because HIV can become resistant to each class of drugs, combination treatment is necessary to effectively suppress the virus. Currently available antiretroviral drugs do not cure HIV infection and they all have side effects that can be severe. A number of drugs are available to help treat the opportunistic infections people with HIV infection tend to develop. These drugs include foscarnet and gancyclovir, used to treat cytomegalovirus eye infections, fluconazole to treat yeast and other fungal infections, and TMP/SMX or pentamidine to treat *Pneumocystis carinii* pneumonia (PCP). HIV-infected individuals who develop Kaposi's sarcoma or other cancers are treated with radiation, chemotherapy, or injections of alpha interferon, a genetically engineered naturally occurring protein.

Clearly, a need exists to develop additional therapies for HIV infection and AIDS treatment that are not subject to viral resistance and that have minimal side effects.

BRIEF SUMMARY OF THE INVENTION

In one aspect, the invention features a method of treating HIV infection in a mammal comprising administering a cytokine antagonist to the mammal such that HIV infection is treated. In a preferred embodiment, the mammal is a human in need of treatment for HIV infection. In another aspect, the invention features treating a subject at risk of HIV infection comprising administering a cytokine antagonist to the subject.

In another embodiment, the cytokine antagonist is an IL-4/IL-13 trap. In still other embodiments, the cytokine antagonist is an IL-4 trap, an IL-13 trap, or anti-IL-4 antibodies or anti-IL-13 antibodies.

In one embodiment, the HIV infection is chronic infection. The chronic infection phase is characterized by multiple antibodies to HIV and a limited Th1/CTL response. In another embodiment, the HIV infection is acute infection. In the acute infection phase, antibodies have not yet developed and individuals, if treated appropriately, have a greater chance to become long-term non-progressors i.e. do not develop AIDS.

In another embodiment of the method of the invention, HIV infection is treated by blocking IL-4- and IL-13-mediated biological effects.

In a second aspect, the invention features a method of augmenting the efficacy of HIV vaccination in a human comprising administering an IL-4/IL-13 antagonist to the human such that the efficacy of HIV vaccination is augmented. In a specific embodiment, the IL-4/IL-13 antagonist is an IL-4/IL-13 trap. In still other specific embodiments, the cytokine antagonist is an IL-4 trap, an IL-13 trap, or anti-IL-4 antibodies or anti-IL-13 antibodies.

In a third aspect, the invention features a method of shifting the HIV vaccination-induced immune response in a human towards a Th1-type response, comprising co-administration of an IL-4/IL-13 antagonist and the vaccine to the human such that the HIV vaccination-induced immune response is shifted towards a Th1-type response. In a specific embodiment, the IL-4/IL-13 antagonist is an IL-4/IL-13 trap. In another specific embodiment, the cytokine antagonist is an IL-4 trap, an IL-13 trap, or anti-IL-4 antibodies or anti-IL-13 antibodies. Another embodiment is a method of treating HIV or AIDS comprising administering the cytokine antagonist, for example IL-4/IL-13 trap, in combination with anti-retroviral therapy, either by co-administraion or alternating administration.

In a fourth aspect, the invention features a method of shifting the Th2-type immune response to a Th1-type immune response in an HIV-infected human comprising administering an IL-4/IL-13 antagonist to the human such that the Th-2-type response is shifted to a Th1-type response in a specific embodiment, the IL-4/1L-13 antagonist is an IL-4/IL-13 trap. In other embodiments, the cytokine antagonist is an IL-4 trap, an IL-13 trap, or anti-IL-4 antibodies or anti-IL-13 antibodies.

In a related fifth aspect, the invention features a method of inhibiting the Th2-type immune response in an HIV-infected human comprising administering an IL-4/IL-13 antagonist to the human such that the Th-2-type response is inhibited. In a specific embodiment, the IL-4/IL-13 antagonist is an IL-4/IL-13 trap and n still other specific embodiments, the cytokine antagonist is an IL-4 trap, an IL-13 trap, or anti-IL-4 antibodies or anti-IL-13 antibodies.

Additional embodiments of the invention include methods wherein the administration is subcutaneous, intramuscular, intranasal, intrathecal, intraarterial, intravenous, topical, transvaginal, transdermal, or transanal administration.

In a sixth aspect, the invention features pharmaceutical compositions comprising an IL-4/IL-13 antagonist of the invention with a pharmaceutically acceptable carrier. Other objects and advantages will become apparent from a review of the ensuing detailed description.

DETAILED DESCRIPTION OF THE INVENTION

Figure 1:
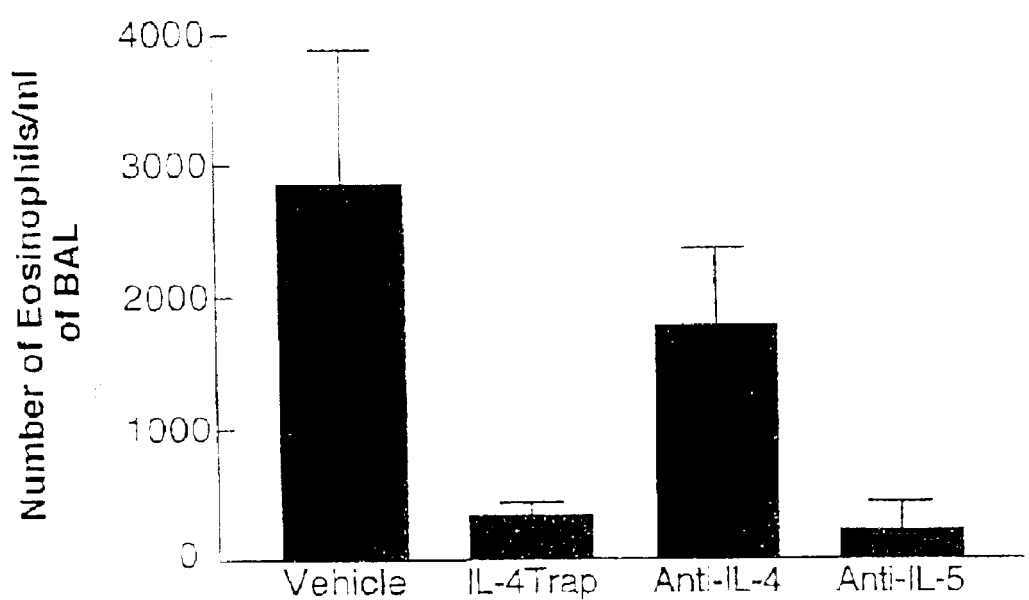
FIG. 1: IL-4 trap blocks in vivo effects of IL-4. Murine IL-4 trap reduces asthma-related eosinophilia in an OVA-induced asthma model in mice. BALB/c mice (n=6 per group) were sensitized to OVA (20 mg per mouse) emulsified with alum on days 0 and 14. Murine IL-4 trap or vehicle was administered at 3 mg/kg SC on the day before sensitization, then 3x/week for 4 weeks, and then daily during the challenge period. The anti-IL-4 and anti-IL-5 antibodies were administered SC once per week at 1 mg/kg. The mice were challenged for 20 minutes with aerosolized OVA (1% for 20 min) on days 28–30. The mice were sacrificed on day 32, and the number of eosinophils in the BAL was quantitated (mean±SEM).

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", an and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

General Description

An object of the present invention is the use of cytokine antagonists in the treatment of cytokine-related diseases or disorders, including HIV infection and AIDS. In particular, Applicants describe herein a novel therapy for treating HIV infection and AIDS that comprises administering to the patient cytokine antagonists that serve to modulate the immune response by promoting a Th1-type immune response, and in particular promoting HIV specific CTL response, that may provide a therapeutic benefit. Specifically, Applicants describe herein a method for treating HIV infection and AIDS comprising administering IL-4/IL-13 antagonists.

HIV disease is characterized by a gradual deterioration of immune function. Most notably, crucial immune cells called $CD4^+T$ cells are disabled and killed during the typical course of infection. These cells, sometimes called "T-helper cells," play a central role in the immune response, signaling other cells in the immune system to perform their functions.

A healthy, uninfected person usually has 800 to 1,200 $CD4^+T$ cells per cubic millimeter ($mm^3$) of blood. During HIV infection, the number of these cells in a person's blood progressively declines. When a person's $CD4^+T$ cell count falls below $200/mm^3$, he or she becomes particularly vulnerable to the opportunistic infections and cancers that typify AIDS, the end stage of HIV infection. A strong HIV-specific CTL response may be the primary mechanism of successful control of the disease.

Therefore, an agent that promotes and drives the immune system to a Th1/CTL response may provide therapeutic benefit in the treatment of HIV disease. Furthermore, reducing the antibody-based Th2 responses may also provide additional overall therapeutic benefit in treating HIV infection.

The invention is based in part on Applicants' novel finding that administration of an agent capable of blocking or inhibiting either or both IL-4 and IL-13-mediated activity favors a Th1 response that is required for the immune control of HIV infection and AIDS. These findings represent the first time an agent capable of blocking or inhibiting IL-4 and/or IL-13-mediated activity has been shown to have these effects. Thus, the invention provides for novel methods of treating HIV infection and AIDS in a mammal by administering an IL-4 and/or IL-13 blocker, in particular, an IL-4/IL-13 trap. In a specific embodiment, an agent capable of blocking IL4-mediated activity is administered. In another specific embodiment, an agent capable of blocking IL-13-mediated activity is administered. In a third specific embodiment, an agent or agents capable of blocking both IL-4 and IL-13-mediated activity is administered. In a fourth specific embodiment, the agent capable of blocking IL-4 is anti-IL-4 antibodies. In a fifth specific embodiment, the agent capable of blocking IL-13 is anti-IL-13 antibodies.

A strong Th1 response to HIV infection is thought to be required for the ultimate control of the HIV infection and AIDS. In fact, the imbalance from a Th1 towards a Th2 response to the viral infection is correlated with poor prognosis. IL-4 and IL-13 are powerful mediators of the Th2 response. Herein, Applicants describe a novel biologic agent that blocks IL-4 and IL-13-mediated biological activity and the resultant Th2 response, thus favoring a Th1 response that is required for the immune control of HIV infection and AIDS.

These agents, termed cytokine traps, are fusions between cytokine receptor components and the Fc portion of IgG. Cytokine traps are a novel extension of the receptor-Fc fusion concept in that they include two distinct receptor components that bind a single cytokine, resulting in the generation of blockers with dramatically increased affinity over that offered by single component reagents. In fact, the cytokine traps that are described herein are among the most potent cytokine blockers ever described. Briefly, the IL-4/IL-13 traps are comprised of the extracellular domain of human IL-13Rα, followed by the extracellular domain of human IL-4Rα, followed by part of the hinge region, the CH2 and CH3 domains of human IgG. Alternatively, the IL-4/IL-13 traps are comprised of the extracellular domain of human IL-14Rα, followed by the extracellular domain of human IL-13Rα, followed by part of the hinge region, the CH2 and CH3 domains of human IgG. For a more detailed description of the IL-4, IL-13 and IL-4/IL-13 traps, see PCT International Application No. PCT/US99/2204, filed Sep. 22, 1999, WO Publication No. 00/18932, in the name of Regeneron Pharmaceuticals, Inc., the contents of which is incorporated herein in its entirety by reference. These IL-4, IL-13 and IL-4/IL-13 traps bind their respective circulating cytokines, rendering these cytokines inactive. The IL-4/IL-13 trap binds IL-4 and IL-13 with Kd values of 20 and 4 pM, respectively, thus blocking the cytokine's signaling.

IL-4 and IL-13 mediate a Th2 antibody immune response, therefore the traps, by blocking IL-4 and IL-13-mediated biological effects, inhibit the Th2 response and sway the immune system towards a Th1/CTL-based response. Since this type of modulation is what best controls HIV replication, these traps provide a therapeutic benefit in the treatment of HIV infection and AIDS.

The cytokine antagonists may be beneficial as a monotherapy or in combination with highly active anti-retroviral therapy (HAART) or in combination with vaccine-based HIV therapeutics. In support of this concept, subjects resistant to HIV infection are associated with a global hyporesponsiveness to IL-4 production (Trivedi, et al., 2001 FASEB 15:1795–97). Furthermore, subjects infected with HIV and that have a polymorphism just upstream from the IL-4 gene are associated with reduced viral load compared to those without this polymorphism, though in this case it is unclear whether this polymorphism blocks IL-4. Applicants contend that a method of blocking IL-4 and/or IL-13 may provide a therapeutic benefit in the treatment of HIV infection and AIDS.

HIV infection has an acute and chronic phase of infection. Most infected individuals are in the chronic phase. The chronic phase is characterized by multiple antibodies to HIV and a limited Th1/CTL response. In the acute phase, antibodies have not yet developed and individuals, if treated appropriately, have a greater chance to become long term non-progressors i.e. do not develop AIDS. It is possible that treatment with cytokine antagonists such as an IL-4, IL-13 or IL-4/13 traps, or anti-IL-4 or anti-IL-13 antibodies, could increase the probability that an individual in the acute phase of infection will become a long term non-progressor.

The methods of the invention comprise administering a therapeutically effective amount of pharmaceutical compositions of a cytokine antagonist, preferably, an IL-4, IL-13 or IL-4/13 traps, or anti-IL-4 or anti-IL-13 antibodies, in an acceptable pharmaceutical carrier, see, infra, to the subject in need, i.e., a subject afflicted with HIV infection or AIDS. In some specific embodiments, the cytokine antagonist, preferably, an IL-4/IL-13 antagonist, more preferably, an IL-4/IL-13 trap, is used to treat patients experiencing the symptoms of HIV infection and AIDS.

Definitions

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

By the term "blocker" or "inhibitor" is meant a substance that retards or prevents a chemical or physiological reaction or response. Common blockers or inhibitors include but are not limited to antisense molecules, antibodies, antagonists, traps, and their derivatives. More specifically, an example of an IL-4 and IL-13 blocker or inhibitor is an IL-4 and IL-13 receptor-based antagonist including, but not limited to, IL-4/IL-13 trap. For a complete description of IL-4/IL-13-receptor based antagonists including IL-4/IL-13 trap, see U.S. Pat. No. 6,472,179, in the name of Regeneron Pharmaceuticals, Inc., the contents of which is incorporated in its entirety herein by reference.

As used herein, the term "HIV infection" generally encompasses infection of a host, particularly a human host, by the human immunodeficiency virus (HIV) family of retroviruses including, but not limited to, HIV I, HIV II, HIV III (also known as HTLV-II, LAV-1, LAV-2), and the like. "HIV" can be used herein to refer to any strains, forms, subtypes, clades and variations in the HIV family. Thus, treating HIV infection will encompass the treatment of a person who is a carrier of any of the HIV family of retroviruses or a person who is diagnosed of active AIDS, as well as the treatment or prophylaxis of the AIDS-related conditions in such persons. A carrier of HIV may be identified by any methods known in the art. For example, a person can be identified as an HIV carrier on the basis that the person is anti-HIV antibody positive, or is HIV-positive, or has symptoms of AIDS. That is, "treating HIV infection" should be understood as treating a patient who is at any one of the several stages of HIV infection progression, which, for example, include acute primary infection syndrome (which can be asymptomatic or associated with an influenza-like illness with fevers, malaise, diarrhea and neurologic symptoms such as headache), asymptomatic infection (which is the long latent period with a gradual decline in the number of circulating CD4$^+$T cells), and AIDS (which is defined by more serious AIDS-defining illnesses and/or a decline in the circulating CD4 cell count to below a level that is compatible with effective immune function). In addition, "treating or preventing HIV infection" will also encompass treating suspected infection by HIV after suspected past exposure to HIV by e.g., contact with HIV-contaminated blood, blood transfusion, exchange of body fluids, "unsafe" sex with an infected person, accidental needle stick, receiving a tattoo or acupuncture with contaminated instruments, or transmission of the virus from a mother to a baby during pregnancy, delivery or shortly thereafter. The term "treating HIV infection" may also encompass treating a person who has not been diagnosed as having HIV infection but is believed to be at risk of infection by HIV.

The term "treating AIDS" means treating a patient who exhibits more serious AIDS-defining illnesses and/or a decline in the circulating CD4 cell count to below a level that is compatible with effective immune function. The term "treating AIDS" also encompasses treating AIDS-related conditions, which means disorders and diseases incidental to or associated with AIDS or HIV infection such as AIDS-related complex (ARC), progressive generalized lymphadenopathy (PGL), anti-HIV antibody positive conditions, and HIV-positive conditions, AIDS-related neurological conditions (such as dementia or tropical paraparesis), Kaposi's sarcoma, thrombocytopenia purpurea and associated opportunistic infections such as Pneumocystis carinii pneumonia, Mycobacterial tuberculosis, esophageal candidiasis, toxoplasmosis of the brain, CMV retinitis, HIV-related encephalopathy, HIV-related wasting syndrome, etc.

Thus, the term "preventing AIDS" as used herein means preventing in a patient who has HIV infection or is suspected to have HIV infection or is at risk of HIV infection from developing AIDS (which is characterized by more serious AIDS-defining illnesses and/or a decline in the circulating CD4 cell count to below a level that is compatible with effective immune function) and/or AIDS-related conditions.

The cytokine antagonists of the invention can be used therapeutically or prophylactically in a subject in need or at risk of HIV infection and AIDS. For example, they can be used to reduce the viral load from an infected subject. Further, the cytokine antagonists of the invention can be used to inhibit the progression to AIDS in an HIV infected subject. Still further, cytokine antagonists can be used prophylactically, e.g., after exposure or suspected exposure to HIV to prevent infection.

Standard methods for measuring in vivo HIV infection and progression to AIDS can be used to determine whether a subject is positively responding to treatment with the HIV-specific fusion protein of the invention. For example, after treatment with a cytokine antagonist of the invention, a subject's T cell count can be monitored. A rise in T cells indicates that the subject is benefiting from administration of the cytokine antagonist. This, as well as other methods known to the art, may be used to determine the extent to which the methods of the present invention are effective at treating HIV infection and AIDS in a subject.

Antisense Nucleic Acids

In a further embodiment, IL-4 and IL-13-mediated activity is blocked or inhibited by the use of IL-4 and IL-13 antisense nucleic acids. The present invention provides the therapeutic or prophylactic use of nucleic acids comprising at least six nucleotides that are antisense to the genes or cDNAs encoding IL-4 and IL-13 or portions thereof of each. As used herein, IL-4 and IL-13 "antisense" nucleic acids refers to nucleic acids capable of hybridizing by virtue of some sequence complementarity to a portion of an RNA (preferably mRNA) encoding either IL-4 or IL-13. The antisense nucleic acids may be complementary to a coding and/or noncoding region of an mRNA encoding either IL-4 or IL-13. Such antisense nucleic acids have utility as compounds that prevent IL-4 and IL-13 expression, and can be used in the treatment of HIV infection and AIDS. The antisense nucleic acids of the invention are double-stranded or single-stranded oligonucleotides, RNA or DNA or a modification or derivative thereof, and can be directly administered to a cell or produced intracellularly by transcription of exogenous, introduced sequences.

The invention further provides pharmaceutical compositions comprising a therapeutically effective amount of IL-4 and IL-13 antisense nucleic acids, and a pharmaceutically acceptable carrier, vehicle or diluent.

The IL-4 and IL-13 antisense nucleic acids are of at least six nucleotides and are preferably oligonucleotides ranging from 6 to about 50 oligonucleotides. In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof and can be single-stranded or double-stranded. In addition, the antisense molecules may be polymers that are nucleic acid mimics, such as PNA, morpholino oligos, and LNA. Other types of antisence molecules include short double-stranded RNAs, known as siRNAs, and short hairpin RNAs, and long dsRNA (>50 bp but usually ≧500 bp).

Short Interfering RNAs

In another embodiment, IL-4 or IL-13 expression is inhibited by a short interfering RNA (siRNA) through RNA interference (RNAi) or post-transcriptional gene silencing (PTGS) (see, for example, Ketting et al. (2001) Genes Develop. 15:2654–2659). siRNA molecules can target homologous mRNA molecules for destruction by cleaving the mRNA molecule within the region spanned by the siRNA molecule. Accordingly, siRNAs capable of targeting and cleaving homologous IL-4 or IL-13 mRNA are useful for treating HIV infection and AIDS.

Inhibitory Ribozymes

In another embodiment, HIV infection and AIDS may be treated in a subject suffering from such disease by decreasing the level of IL-4 and IL-13 activity by using ribozyme molecules designed to catalytically cleave gene mRNA transcripts encoding IL-4 or IL-13, preventing translation of target gene mRNA and, therefore, expression of the gene product.

Ribozymes are enzymatic RNA molecules capable of catalyzing the specific cleavage of RNA. The mechanism of ribozyme action involves sequence-specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246. While ribozymes that cleave mRNA at site-specific recognition sequences can be used to destroy mRNAs encoding IL-4 or IL-13, the use of hammerhead ribozymes is preferred. Hammerhead ribozymes cleave mRNAs at locations dictated by flanking regions that form complementary base pairs with the target mRNA. The sole requirement is that the target mRNA has the following sequence of two bases: 5'-UG-3'. The construction and production of hammerhead ribozymes is well known in the art. The ribozymes of the present invention also include RNA endoribonucleases (hereinafter "Cech-type ribozymes") such as the one that occurs naturally in *Tetrahymena thermophila* (known as the IVS, or L-19 IVS RNA). The Cech-type ribozymes have an eight base pair active site that hybridizes to a target RNA sequence where after cleavage of the target RNA takes place. The invention encompasses those Cech-type ribozymes that target eight base-pair active site sequences that are present in the genes encoding IL-4 and IL-13.

Generation of Antibodies to IL-4 and IL-13 Proteins

In another embodiment, HIV infection and AIDS may be treated in a subject suffering from such disease by decreasing the level of IL-4 and IL-13 activity by using antibodies against IL-4 or IL-13. The term "antibody" as used herein refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant regions, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Within each IgG class, there are different isotypes (eg. $IgG_1$, $IgG_2$, etc.). Typically, the antigen-binding region of an antibody will be the most critical in determining specificity and affinity of binding.

An exemplary immunoglobulin (antibody) structural unit comprises a tetramer. Each tetramer is composed of two identical pairs of polypeptide chains, each pair having one light chain (about 25 kD) and one heavy chain (about 50–70 kD). The N-terminus of each chain defines a variable region of about 100–110 or more amino acids primarily responsible for antigen recognition. The terms "variable light chain" ($V_L$) and variable heavy chain ($V_H$) refer to these light and heavy chains respectively.

Methods for preparing antibodies are known to the art. See, for example, Kohler & Milstein (1975) Nature 256:495–497; Harlow & Lane (1988) *Antibodies: a Laboratory Manual*, Cold Spring Harbor Lab., Cold Spring Harbor, N.Y.). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity. Techniques for the production of single chain antibodies or recombinant antibodies (U.S. Pat. No. 4,946,778; U.S. Pat. No. 4,816,567) can be adapted to produce antibodies used in the fusion proteins and methods of the instant invention. Also, transgenic mice, or other organisms such as other mammals, may be used to express human or humanized antibodies. Alternatively, phage display technology can be used to identify antibodies and heteromeric Fab fragments that specifically bind to selected antigens.

Antibody Screening and Selection

Screening and selection of preferred antibodies can be conducted by a variety of methods known to the art. Initial screening for the presence of monoclonal antibodies specific to a target antigen may be conducted through the use of ELISA-based methods, for example. A secondary screen is preferably conducted to identify and select a desired monoclonal antibody for use in construction of the multi-specific fusion proteins of the invention. Secondary screening may be conducted with any suitable method known to the art. One preferred method, termed "Biosensor Modification-Assisted Profiling" ("BiaMAP") is described in co-pending U.S. Ser. No. 60/423,017 filed Nov. 1, 2002, herein specifically incorporated by reference in its entirety. BiaMAP allows rapid identification of hybridoma clones producing monoclonal antibodies with desired characteristics. More specifically, monoclonal antibodies are sorted into distinct epitope-related groups based on evaluation of antibody:antigen interactions.

Methods of Administration

The invention provides methods of treatment comprising administering to a subject an effective amount of an agent of the invention. In a preferred aspect, the agent is substantially purified (e.g., substantially free from substances that limit its effect or produce undesired side-effects). The subject is preferably an animal, e.g., such as cows, pigs, horses, chickens, cats, dogs, etc., and is preferably a mammal, and most preferably human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429–4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration may be acute or chronic (i.e. daily, weekly, monthly, etc.). Such administration may be alone or in combination with other agents. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, fibers, or commercial skin substitutes. In addition, pre-treatment of a tissue or organ with the agent prior to transplant of such tissue or organ may be desirable.

In another embodiment, the active agent can be delivered in a vesicle, in particular a liposome (see Langer (1990) Science 249:1527–1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cellsurface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid can be introduced intracellularly and incorporated within host cell DNA for expression, by homologous recombination.

Combination Therapies

In numerous embodiments, the fusion proteins of the present invention may be administered in combination with one or more additional compounds or therapies. For example, multiple fusion proteins can be co-administered, or one or more fusion proteins can be administered in conjunction with one or more therapeutic compounds. For example, the other therapeutic agent may be nucleoside analog reverse transcriptase inhibitors (NRTIs) including zidovudine (AZT), zalcitabine (ddC), didanosine (ddI), stavudine (D4T), lamivudine (3TC) and abacavir succinate. In addition, the other therapeutic agent may be non-nucleoside reverse transcriptase inhibitors (NNRTIs) such as delavirdine, nevirapine and efavirenz. In addition, the other therapeutic agent may be protease inhibitors including ritonavir, saquinivir, indinavir, amprenavir, lopinavir and nelfinavir. The last class used in combination might be fusion inhibitors, such as T-20. In addition, the other therapeutic agent may be a drug to help treat the opportunistic infections people with HIV infection tend to develop. These drugs include foscarnet and gancyclovir, used to treat cytomegalovirus eye infections, fluconazole to treat yeast and other fungal infections, and TMP/SMX or pentamidine to treat *Pneumocystis carinii* pneumonia (PCP). Also, therapeutic agents or treatment modalities to treat Kaposi's sarcoma or other cancers are radiation, chemotherapy, or injections of alpha interferon, a genetically engineered naturally occurring protein and be co-administered with the fusion proteins of the present invention.

Pharmaceutical Compositions

The present invention also provides pharmaceutical compositions. Such compositions comprise a therapeutically effective amount of an active agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. In a preferred embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the active agent of the invention that will be effective in the treatment of delayed-type hypersensitivity can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration, and the judgment of the prescribing physician.

The therapy may be repeated intermittently while symptoms are detectable or even when they are not detectable. The therapy may be provided alone or in combination with other drugs.

Preferably, a therapeutically effective dose of the compounds described herein will provide therapeutic benefit without causing substantial toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds that exhibit high therapeutic indices are preferred. The data obtained from these cell culture assays and animal studies can be used in formulating a dosage range that is not toxic for use in humans. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch.1, p.1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administered dose in the management of the clinical disorder of interest will vary with the severity of the condition to be treated and the route of administration. The severity of the condition may, for example, be evaluated, in part, by appropriate prognostic evaluation methods. Further, the dose and perhaps dose frequency, will also vary according to the age, body weight, and response of the individual patient.

EXAMPLES

Example 1
IL-4/IL-13 Trap can Shift the Immune Response from a Th2-type Response to a Th1-type Response Balb/c mice (which have a tendency towards a Th2-type response) were sensitized and then challenged by intranasal delivery of ovalbumin (OVA), to create a condition that is similar to human asthma. This includes high levels of IgE (a Th2-type response marker) and high eosinophilia (induced by IL-5, a Th2 cytokine). The effects of administration of the IL-4/IL-13 trap during the challenge phase of the model has been assessed by microarrays. The RNA from the lungs from mice that were treated with either human Fc or mouse IL-4/13 trap was analyzed. It was found that several genes that are regulated by IL-4 and IL-13 were reduced by the presence of the IL-4/IL-13 trap but not by human Fc. More importantly, IFN gamma and IL-18 were only detectable in the RNAs from the IL-4/IL-13 trap-treated animals. This indicates that, not only had a Th2-type immune response been reduced, but that there was also an induction of a Th1-type response by the administration of the IL-4/IL-13 trap.

Example 2
IL-4 Trap can Shift the Immune Response from a Th2-type Response to a Th1-Type Response Since human IL-4 is not cross-reactive in rodents, Applicants could not investigate the efficacy of human IL-4 trap in mouse models. Therefore, Applicants engineered a murine version of the IL-4 trap and evaluated its ability to block IL-4 in an ovalbumin (OVA)-induced asthma model in mice. IL-4 plays a critical role in generating Th2 immune responses and activated Th2 cells secrete a variety of cytokines, including IL-5, which play a pivotal role in the eosinophilia observed in the asthma phenotype. Elevated numbers of eosinophils are observed in the bronchial-alveolar lavage (BAL) fluid of OVA-treated mice. Administration of murine IL-4 trap prior to sensitization and continuing through the challenge period significantly reduced the levels of eosinophils indicating that the IL-4 trap blocks the IL-4-mediated activation of Th2-type responses in vivo (FIG. 1). In order to evaluate the clinically relevant human IL-4 trap, Applicants assessed its ability to block IL-4 action in primates. Subcutaneous administration of human IL-4 to cynomologus monkeys over the course of 4 days results in a variety of biological responses, including increases in hematocrit and serum levels of the chemokine MCP-1. Importantly, prior administration of the IL-4 trap blocked both the IL-4 mediated induction of MCP1 and the increase in hematocrit. These results establish that the human IL-4 trap is capable of blocking IL-4 action in vivo.

Example 3
Murine IL-4/IL-13 Trap can Inhibit In Vivo IgE Responses

Injection of mice with monoclonal anti-mouse IgD antibodies leads to the activation of both B and T cells and the subsequent secretion of IgE into the circulation in an IL-4-mediated manner (Sato et al, J. Immunology, 1993, 150:2717–2723). Previous studies have indicated that treatment with anti-IL4 antibodies can inhibit the IgE response to anti-IgD antibodies (Sato et al, J. Immunology, 1993, 150:2717–2723). Therefore, this model can be used to evaluate the efficacy of various "anti-IL-4" therapeutics, including the murine IL-4/IL-13 trap which can bind both murine IL-4 and murine IL-13 cytokines, in blocking an IL-4-mediated event.

Female BALB/c mice (9 weeks of age; Taconic) were given a subcutaneous injection of rat anti-mouse IgD monoclonal antibody (200 µg; Biosource) or PBS on Day 0. Animals receiving the anti-IgD antibody were injected subcutaneously twice a day (Days 1–8) with placebo or murine IL-4/IL-13 trap (16 to 64 mg/kg/day; 8 to 32 mg/kg/injection); other mice were injected with an anti-murine IL-4 antibody (11B11; 30 µg/day, sc; Days 1–8). Mice who received PBS on Day 0 were injected sc with placebo during this time frame. Blood samples were taken on Day 9 and the sera were assayed for IgE levels using the OptEIA Mouse IgE ELISA kit (PharMingen).

Figure 2:
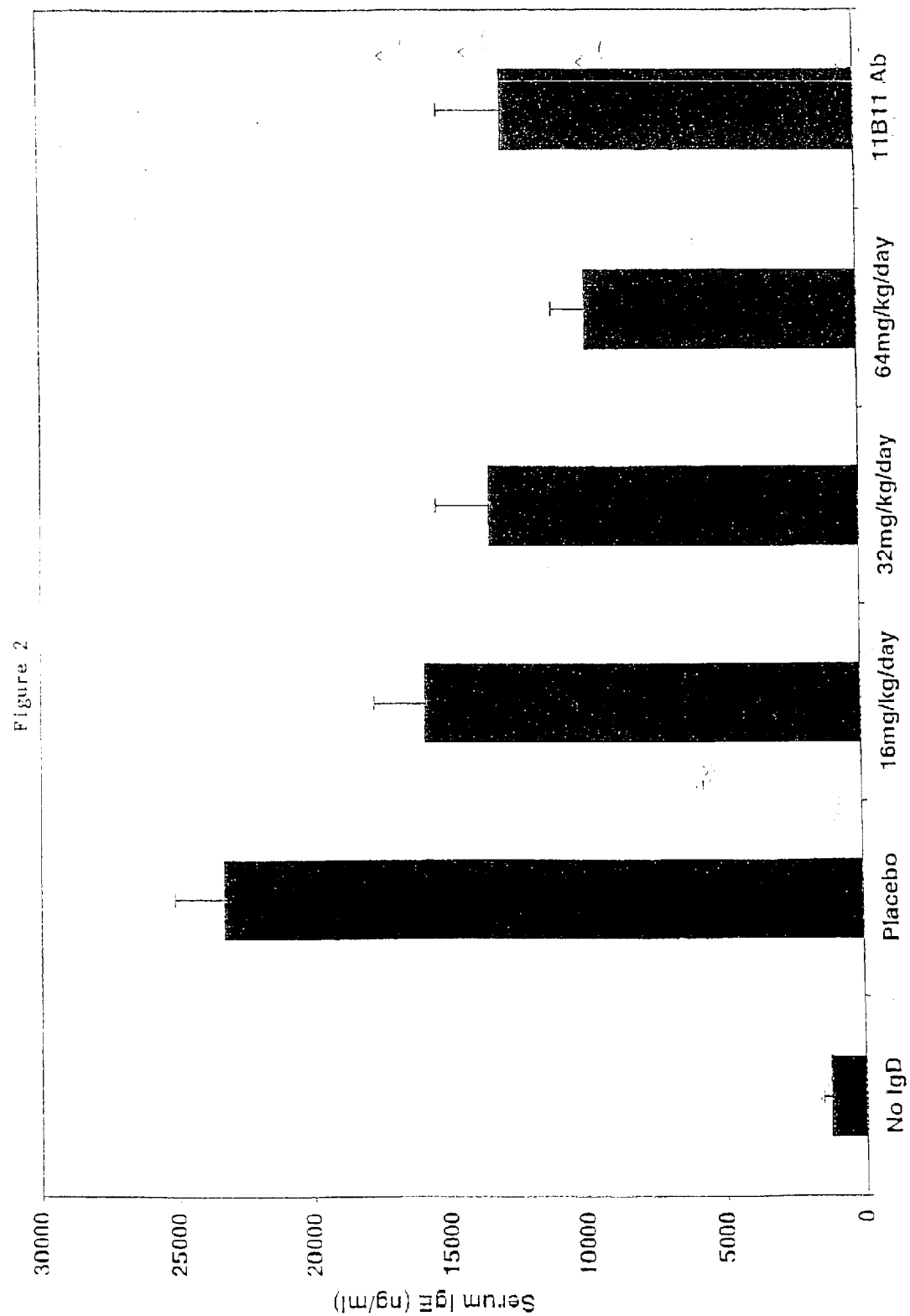
FIG. 2: Murine IL-4/IL-13 trap can inhibit in vivo IgE responses. Female BALB/c mice were given a subcutaneous injection of rat anti-mouse IgD monoclonal antibody (200 µg) or PBS on Day 0. Animals receiving the anti-IgD antibody were injected subcutaneously twice a day (Days 1–8) with placebo or murine IL-4/IL-13 trap (16 to 64 mg/kg/day; 8 to 32 mg/kg/injection); other mice were injected with an anti-murine IL-4 antibody (11B11; 30 µg/day, sc; Days 1–8). Mice who received PBS on Day 0 were injected sc with placebo during this time frame. Blood samples were taken on Day 9 and the sera were assayed for IgE levels using the OptEIA Mouse IgE ELISA kit. Exogenous administration of anti-mouse IgD antibodies significantly increased serum IgE levels relative to PBS-injected controls. Treatment with murine IL-4/IL-13 trap significantly reduced serum IgE levels compared to placebo in an apparent dose-dependent manner. An anti-mouse IL-4 antibody (11B11) was also effective at reducing serum IgE levels.

Exogenous administration of anti-mouse IgD antibodies significantly increased serum IgE levels relative to PBS-injected controls (FIG. 2). Treatment with murine IL-4/IL-13 trap significantly reduced serum IgE levels compared to placebo in an apparent dose-dependent manner (FIG. 2). An anti-mouse IL-4 antibody (11B11) was also effective at reducing serum IgE levels. This data indicates that the murine IL-4/IL-13 trap can block IL-4-mediated events in an in vivo setting.

IL-4/IL-13 trap, administered as a subcutaneous injection (3 mg/kg) to cynomologus monkeys, has excellent pharmacokinetic properties (Cl/F=3.4±0.8 ml/h/kg, Cmax=17±4 ug/ml, and $t_{1/2}$=29±2 h) that may translate into weekly dosing in humans. A murine version of the IL-4/IL-13 trap markedly reduced the anti-IgD induced, Th2 driven B-cell switch to IgE production in mice, demonstrating a block of this IL-4 driven Th2 response in vivo. Administration of the human IL-4/IL-13 trap blocked the airway hyper-reactivity induced upon the instillation of human IL-13 to mouse lungs, demonstrating IL-13 signal blocking in vivo. The human IL-4/IL-13 trap was also well tolerated in a six-week toxicology study in cynomologus monkeys that were subcutaneously administered up to 10 mg/kg of the trap twice-weekly. From these results, Applicants propose that the IL-4/IL-13 trap may be useful for the treatment of HIV either alone or in combination with other chemotherapeutic agents in all phases of infection. The trap may also be useful to enhance the immune response in combination with HIV vaccine therapies.

We claim:

1. A method of reducing a Th2-type immune response in a mammal comprising administering a cytokine antagonist to the mammal such that a Th2-type response is reduced.

2. The method of claim 1 wherein the mammal is a human.

3. The method of claim 1 wherein the cytokine antagonist is selected from the group consisting of an IL-4/IL-13 trap, an IL-4 trap, an IL-13 trap, an anti-IL-4 antibody, and an anti-IL-13 antibody.

4. The method of claim 1 wherein the administration is subcutaneous, intranfuscular, intranasal, intraarterial, intravenous, topical, transvaginal, transdermal, or transanal administration.

5. A method of increasing a Th1-type immune response in a human comprising administering a cytokine antagonist to the human such that a Th1-type immune response is increased.

6. The method of claim 5 wherein the cytokine antagonist is selected from the group consisting of an IL-4/IL-13 trap, an IL-4 trap, an IL-13 trap, an anti-IL-4 antibody, and an anti-IL-13 antibody.

7. The method of claim 5 wherein the administration is subcutaneous, intramuscular, intranasal, intraarterial, intravenous, topical, transvaginal, transdermal, or transanal administration.

8. A method of shifting the Th2-type immune response to a Th1-type immune response in a mammal, comprising administering a cytokine antagonist such that the Th-2-type response is shifted to a Th1-type response.

9. The method of claim 8 wherein the cytokine antagonist is selected from the group consisting of an IL-4/IL-13 trap, an IL-4 trap, an IL-13 trap, an anti-IL-4 antibody, and an anti-IL-13 antibody.

10. The method of claim 8 wherein the administration is subcutaneous, intramuscular, intranasal, intraarterial, intravenous, topical, transvaginal, transdermal, or transanal administration.

11. A method of inhibiting asthma in a mammal, comprising administering a cytokine antagonist such that asthma inhibited.

12. The method of claim 11 wherein the cytokine antagonist is selected from the group consisting of an IL-4/IL-13 trap, an IL-4 trap, an IL-13 trap, an anti-IL-4 antibody, and an anti-IL-13 antibody.

13. The method of claim 11 wherein the administration is subcutaneous, intramuscular, intranasal, intraarterial, intravenous, topical, transvaginal, transdermal, or transanal administration.

* * * * *